United States Patent [19]

Joutel et al.

[11] Patent Number: 5,714,319
[45] Date of Patent: Feb. 3, 1998

[54] METHOD FOR THE SCREENING OF FAMILIAL HEMIPLEGIC MIGRAINE (FHM)

[75] Inventors: Anne Marie Gisèple Joutel; Marie-Germaine Madeleine Bousser; Elisabeth Andrée Tournier-Lasserve, all of Paris, France

[73] Assignee: Institut National de la Sante et de la Recherche Medicale, Paris, France

[21] Appl. No.: 203,194

[22] Filed: Feb. 28, 1994

[51] Int. Cl.⁶ .............................. C12Q 1/68; C12P 19/34
[52] U.S. Cl. .................................. 435/6; 435/91.2
[58] Field of Search ..................... 435/7, 91.2; 935/77, 935/78

[56] References Cited

PUBLICATIONS

Joutel et al; NatureGenetic 1993 V. 5, pp. 40–45.
Biotech. Bus. News (Biosis Abstract).

*Primary Examiner*—Eggerton A. Campbell
*Attorney, Agent, or Firm*—Larson & Taylor

[57] ABSTRACT

Method for screening for familial hemiplegic migraine which comprises searching for the presence of a mutated gene responsible for familial hemiplegic migraine on the chromosome 19, in the region comprised between the microsatellites D19S216 and D19S215, of a family or of an at risk individual, including fetus.

5 Claims, 5 Drawing Sheets

METHOD FOR THE SCREENING OF FAMILIAL HEMIPLEGIC MIGRAINE (FHM)

The present invention relates to a method for the diagnosis of Familial Hemiplegic Migraine (FHM)

BACKGROUND OF THE INVENTION

Migraine is an extremely frequent, and sometimes incapacitating condition, affecting about 4% of children, 6% of men and 18% of women (Stewart, W. F. et al., Jama 267, 64–69, 1992, and Lance J. W., Mechanism and management of headache, fourth ed. Butterworths Scientific, London, 1982). Its etiology is unknown and its pathophysiology poorly understood. In the complete absence of laboratory diagnostic tests, its diagnosis remains purely clinical, based on the detailed description of symptoms by the patient. Until recently, there has been a marked interobserver diagnostic variability due to the lack of explicit definition and precise diagnostic criteria. This has led the experts of the International Headache Society (I.H.S.) to propose a new classification for headache disorders which provides, for the first time, operational diagnostic criteria for all varieties of facial pain and headache, including migraine (Headache Classification Committee of the International Headache Society—Classification and diagnostic criteria for headache disorders, cranial neuralgias and facial pain—Cephalalgia 8, Supplt 7, 19–28, 1988). The two most frequent varieties are migraine without aura (formerly called "common" migraine), and migraine with aura (formerly called "classical" migraine) in which neurological symptoms precede or accompany the headache.

Familial hemiplegic migraine (FHM) is considered in the I.H.S. classification as a subtype of migraine with aura, particular by its rarity, its autosomal dominant pattern of transmission and by the presence of hemiplegia as the salient feature of the aura (Blau, J. N. et al., Lancet 2, 1115–1116, 1955). Since its first description by Clarke in 1910 (Clarke, J. M., Br. Med. J. 1, 1534–1538, 1910), it has been reported in around forty families. The age of onset varies from 5 to 30 years with a predominance during youth. Minor head trauma and cerebral angiography are well established triggering factors (Blau, J. N. et al.—see above—and Glista, G. et al., Mayo Clin. Proc. 50, 307–311, 1975). Attacks are characterized by the presence of an hemiparesis or hemiplegia either isolated or associated with other aura symptoms such as hemianopic blurring of vision, unilateral paresthesiae or numbness, and dysphasia (Whitty, C. W. M., J. Neurol. Neurosurg. Psychiatry 16, 172–177, 1953). These symptoms usually last 30 to 60 minutes and are followed by a severe pulsatile headache lasting a few hours or days. In severe attacks, hemiplegia is often associated with fever, drowsiness, confusion or coma which usually also resolve within a few hours, days or sometimes weeks (Münte, T. F. et al., J. Neurol. 237, 59–61, 1990, and Fitzimons, R. B. et al., Brain 108, 555–557, 1985).

Various combinations of neurological deficits have been described in association with FHM: retinitis pigmentosa, sensorineural deafness, (Young, G. F. et al., Arch. Neurol. 23, 201–209, 1970), essential tremor, disordered ocular smooth poursuit (Zifkin, B. et al., Ann. Neurol. 8, 329–332, 1980). The most frequent one is a progressive cerebellar disturbance with dysarthria, horizontal nystagmus and limb incoordination (Ohta, M. et al., Neurology 17, 813–817, 1967, and Codina, A. et al., Rev. Neurol. (Paris) 124, 526–530, 1971). These deficits are permanent and not part of the aura.

SUMMARY OF THE INVENTION

During the clinical investigation of patients affected with another autosomal dominant neurological condition, CADASIL, the Applicant noticed that some of the patients also experienced recurrent attacks of severe headache, with various aura symptoms including transient hemiplegia (Tournier-Lasserve H. et al., Stroke 22, 1297–1302, 1991). This led the Applicant to raise the hypothesis that CADASIL and FHM, though clinically widely different, might be due to the alteration of the same gene (Tournier-Lasserve B. et al., Nature Genetics, vol. 3, 256–259, March 1993 and Joutel A. et al., Nature Genetics, vol. 5, 40–45, September 1993, which are both incorporated therein by reference). The Applicant performed linkage analysis on 2 unrelated FHM families with a set of DNA markers spanning the most probable location of CADASIL and establish the most likely location of the FHM gene on chromosome 19, within a 30 cM interval encompassing the most probable location of the CADASIL gene. Locus assignment provides the first biological marker for this disease.

Clinical heterogeneity of FHM was reported on the basis of the presence of a cerebellar involvement occuring in some families. In the reference herein enclosed (A. Joutel et al, Nature Genetics, 1993, 5, 40–46) the applicant demonstrated linkage to chromosome 19 in 2 pedigrees of both types (with and without cerebellar involvement).

The Applicant have now studied by linkage analysis more than ten families affected with FHM and established genetic heterogeneity in the sense that approximately fifty percent only of the FHM families tested map on chromosome 19 (A. Joutel, manuscript in preparation). To our current knowledge, these is no clinical difference between chromosome 19 linked and unlinked families.

The invention has several objects:

One object of the invention is to provide a method for diagnosing a subgroup of FHM.

Another object of the invention is to provide a method to estimate the carrier risk for an at risk individual within an affected family linked to chromosome 19.

Another object of the invention is to provide a method to identify FHM families which are linked to chromosome 19 allowing selection of genetically homogenous groups of FHM families, this being potentially important in terms of therapeutic trials.

Another object of the invention is to provide a method for screening families affected with other types of migraine, with and without aura.

These objectives are attained by a method for the genotypic diagnosis of FHM, by searching the presence of a mutated gene responsible for the disease, comprising the search of the presence of a mutation responsible for FHM on the chromosome 19, in the region of it comprised between the microsatellites D19S216 and D19S215, particularly of a family or of an at risk individual, including fetus. Preferably, this method is based on genetic linkage analysis of human samples belonging to the members of the affected families to be tested. The first step is to establish linkage of the disease gene responsible for the disease present in the family with the FHM locus. Linkage analysis is conducted on families which structure is suitable for such analysis, namely families comprising multiple individuals which clinical status (healthy or affected) has been unambiguously established (see Nature Genetics, 1993, 5, 40–46).

Genetic linkage analysis is preferably conducted with a set of highly polymorphic DNA markers (microsatellites flanking highly polymorphic CA or GATA repeats) spanning the most likely location intervals of FHM, flanking markers being D19S216 and D19S215.

Markers are selected to give the best information for a given family. Markers located on both sides of the gene increase the accuracy of the diagnosis and permits the reduction of the risks of false diagnosis in case of recombination. These markers include D19S216, D19S76, D19S221, D19S179, D19S226, D19S252, D19S253, D19S244, D19S415, D19S199, D19S215.

These microsatellites are described in the microsatellites Genethon map (Weissenbach J. & al., Nature 359, 794–801, 1992 which is incorporated therein by reference) as well as in J. Weber et al, Am. J. Hum. Gen. 1993, 53, 1079–1095. The oligonucleotide sequences serving as primers, which are specific of each microsatellite, are available in the Genome Data Bank (Accessing GDB™ and OMIM™ at Johns Hopkins University, Baltimore, Md., USA).

Preferably, the method comprises hybridization of selected primers to the DNA to be tested, followed by DNA amplification by Polymerase Chain Reaction amplification. Preferably, the polymorphic amplified fragments so called amplimers, are then separated according to their size by electrophoresis on acrylamide denaturing gels, blotted on nylon membranes and hybridized with CA12mer or GATA 5mer radiolabelled probes. Data obtained from autoradiographies are computed and Lod-score calculations are carried out using the M-LINK program (Lathrop et al, P.N.A.S., 1984, 81, 3443–3446.). Based on MRI data, penetrance has been established to be complete after 35 years old (see above).

The assertion of linkage or absence of linkage is derived from statistical analysis, a lod-score above 3 establishing unambiguous linkage of the disease gene to the tested marker. A lod-score value of 3 is in fact needed only when the prior probability of linkage between a disease gene and a marker is no more than random, which is not anymore the case for FHM. The strictness of this criterion should be soon decreased according to the prior probability values observed in ongoing epidemiological studies.

Once genotypic analysis has established linkage to chromosome 19 within a given FHM affected family, genotypic analysis can be used in a second step for testing of at risk individuals, members of an affected family for example for predictive testing or help for differential diagnosis when needed. Using linked polymorphic markers a DNA based carrier risk can be calculated using the MLINK program (Lathrop et al, P.N.A.S., 1984, 81, 3443–3446.).

Thus, the preferred general method with respect to the kind of diagnosis comprises hybridyzing DNA fragments from an individual with selected primer pairs which hybridize selectively on DNA sequences flanking allelic DNA polymorphisms situated in the said region comprised between the microsatellites D19S216 and D19S215, including the latter, separately amplifying the DNA polymorphisms flanked by the primers thus forming so-called amplimers and analyzing these polymorphisms in order to assess the presence or absence of linkage or the DNA polymorphism carrier risk by genetic linkage analysis.

The discovery by the inventors that the FHM gene was linked to a specific region of chromosome 19 rendered the principle of a genotypic diagnostic method available. It is evident that from this information and the DNA polymorphisms disclosed therein, it is easy for the specialist to test other markers which would be tested or discovered later. The application of other markers in the genotypic diagnosis of FHM remains within the scope of the present invention.

Besides, on the basis of the therein-disclosed microsatellites, it is easy to search other polymorphisms which are closer to the gene responsible for FHM. The method consists in the search of new polymorphisms which are linked to at least one of the microsatellites disclosed herein. The potential polymorphisms can be then submitted to a linkage analysis in relation with the gene, in order to determine the genetic distances and the Lod Scores.

Therefore, another object of the invention is to propose a method for selecting polymorphisms which are closely related to the gene responsible for FHM, wherein, with the aid of DNA probes, one searches polymorphisms and then one submits these polymorphisms to a linkage analysis with the microsatellites D19S216, D19S76, D19S221, D19S179, D19S226, D19S252, D19S253, D19S244, D19S415, D19S199, D19S215. Thereafter, one can proceed with a linkage analysis of the selected polymorphisms with respect to the disease gene.

DETAILED SPECIFICATION

For the purpose of the present genetic study, the Applicant selected 2 large FHM pedigrees satisfying the I.H.S. criteria for FHM, one with cerebellar signs, the other without. The Applicant performed linkage analysis with a set of DNA markers spanning the best estimate location interval for CADASIL, which was recently mapped on chromosome 19 (Tournier-Lasserve, B. et al., Nature Genetics 3, 256–259, 1993). Linkage of FHM gene was established to two markers, D19S221 and D19S226, with respective maximum lod-scores of 8.24 and 8.07 at $\theta$=0.03. Multilocus analysis localizes the disease gene within the 30 cM (centiMorgans) region located between the D19S216 and the D19S215 loci; this region encompasses the interval spanned by D19S221–D19S215, which is estimated to be the most likely location of CADASIL. Although at present it cannot be excluded heterogeneity, these results suggest that these two diseases may be due to the alteration of the same gene.

Clinical Evaluation

Figure 1:
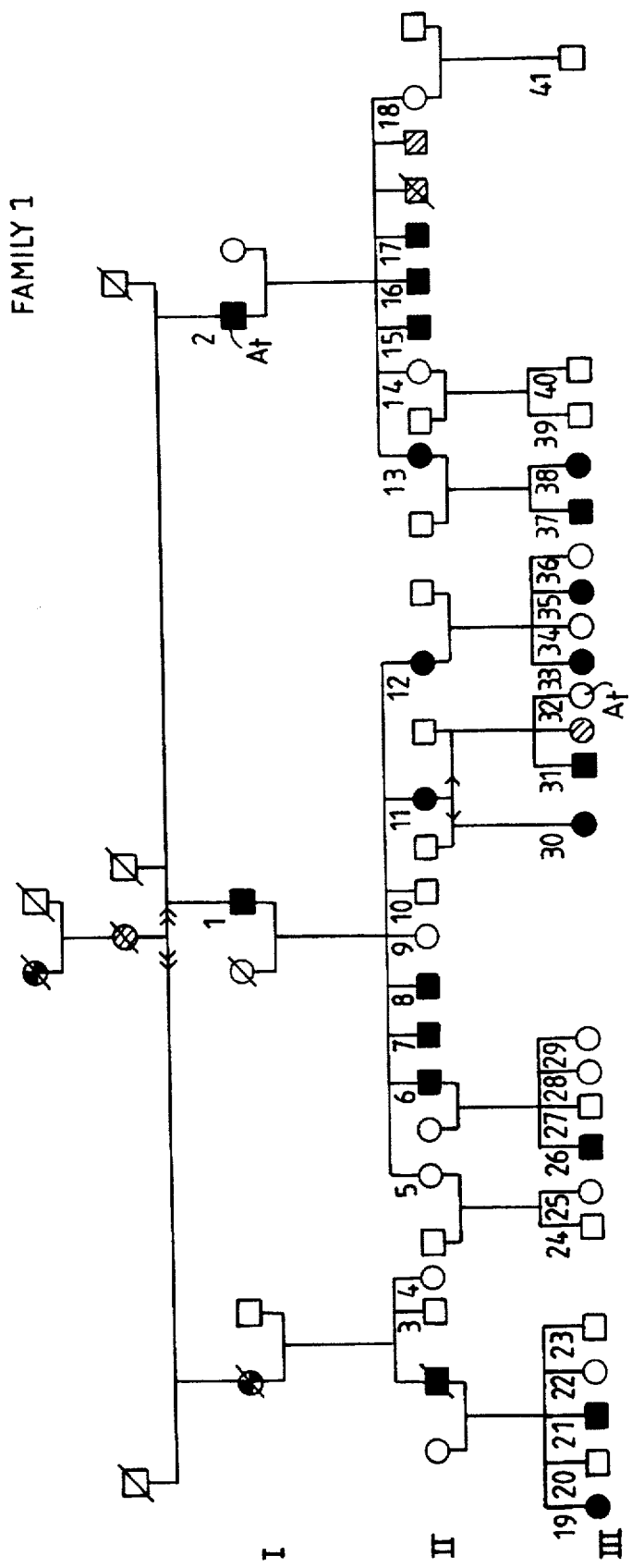
FIG. 1: Pedigree of the first FHM family analyzed. The Roman numbers, on the left, represent the generations, the numbers above the symbols identify the individuals. Squares, males; circles, females; the affected subjects are represented by a filled symbol and by a half-filled symbol when the symptoms are assumed on the basis of familial history; hatched symbols stand for subject of unknown status; At, cerebellar ataxia.

The first pedigree (Family 1, FIG. 1) is a three generation Caucasian family originating from the center of France. All three members from generation I were born most likely of different fathers but of the same mother for whom clinical history was not available. The grandmother on their mother's side was said to have presented recurrent attacks of transient hemiplegia with headache. Thirty eight members of this family were examined and clinical data from three other affected members were obtained by telephone.

Twenty members have experienced attacks of hemiplegic migraine satisfying I.H.S. diagnostic criteria for FHM. Attacks started at a mean age of 17.5 years (range 7–37) in generation II, and 12.1 years (5–26) in generation III. All the patients presented typical hemiplegic attacks and eight of them occasionally had severe attacks in which hemiplegia was associated with confusion or coma and fever. All symptoms always resolved without sequelae. Neurological examination during non-affected periods disclosed horizontal gaze nystagmus in 16 of these affected members and cerebellar ataxia in one (I-2). Mental retardation was present in another individual (III-21). Magnetic resonance imaging (MRI) of the brain, performed on ten subjects (five of them with severe attacks), did not show any abnormal signal. There were no lesions suggestive of infarcis and the brain white matter was normal. A cerebellar vermian atrophy was present in two subjects (I-2, III-21). Cerebral angiography, performed in four individuals, was normal in three, however in one subject (II-7), who had suffered from subarachnoid hemorrhage, a large middle cerebral artery aneurysm was found. In one patient (II-6), two extremely severe attacks were triggered, first, by a coronary arteriorgraphy and second, by a cerebral angiography. Attacks were triggered by minor head trauma in two other patients.

Sixteen other members, with a mean age of 41.8 years (28–50) at generation II and 23.4 (18–35) at generation III, born of an affected parent, were free of attacks of hemiplegic migraine. Neurological examination was normal in 14 of these subjects but disclosed cerebellarataxia and mental retardation in one individual (III-32) and horizontal gaze nystagmus in another (III-28)

Figure 2:
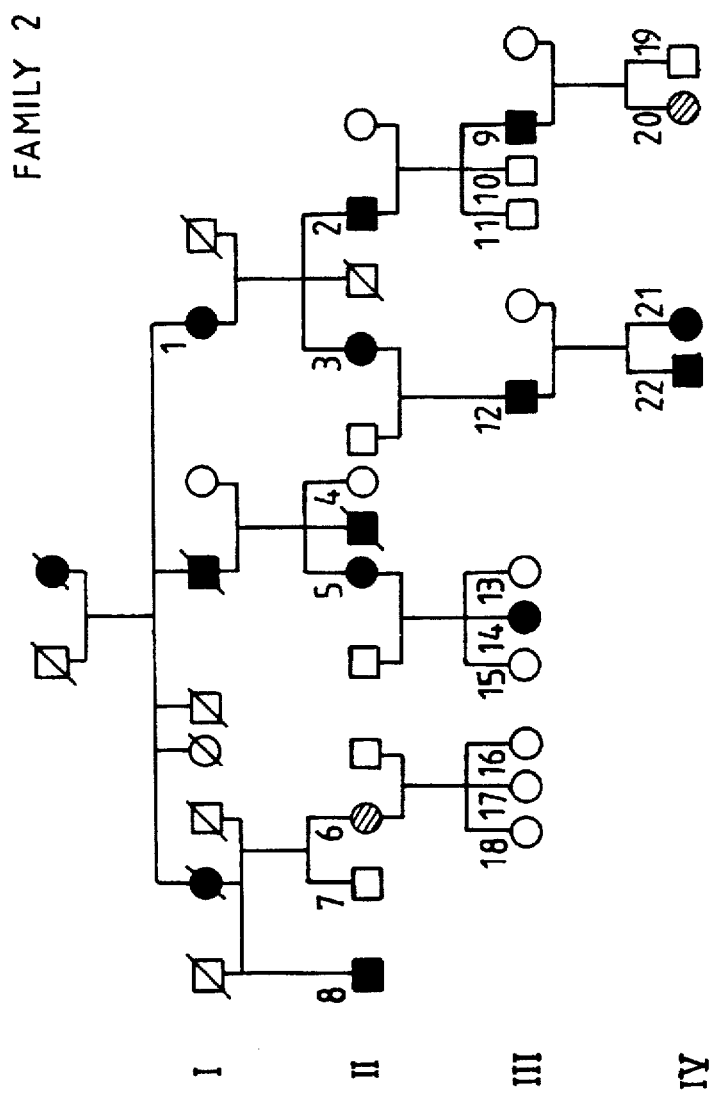
FIG. 2: analogous to FIG. 1 for the second FHM family.

The second pedigree (Family 2, FIG. 2), originates from the south of France. It includes 22 living members, belonging to four generations. Ten have presented typical recurrent attacks of hemiplegic migraine which were occasionally severe in three. Two others have experienced a single episode of respectively transient hemiplegia without headache (II-6) and prolonged hyperthermic confusion (III-20). The mean age of onset was 10.2 years (6–15). Neurological examination performed in eight affected members and two healthy individuals was unremarkable. In particular there was no nystagmus or cerebellar ataxia. Brain MRI and cerebral angiography performed in one subject (III-9) were normal.

Linkage Analysis

The genetic linkage analysis was undertaken on fifty-four members from the two families. Four highly polymorphic markers spanning the region containing the CADASIL locus on chromosome 19 were chosen for genotype characterization. Allele frequencies were estimated initially from data on the CBPH panel (CBPH database version 6). The analysis was repeated with a frequency estimated from the FHM families. Individuals were considered affected for linkage analysis, based on the occurrence of at least one hemiplegic migraine attack as defined by the I.H.S. criteria. Initially, due to uncertainty concerning penetrance, the disease status was included only for affected members, all others being considered of unknown phenotype. As a second step, healthy individuals with a normal neurological examination were considered as non-affected, and included in the analysis. Family 1 included 20 affected members and 11 non-affected members, and family 2 included 10 affected members and 2 non-affected members. Based on data published previously from all families, the penetrance for FHM was estimated to be approximately 0.9.

Significant evidence of linkage was obtained when either affected family members alone, or both affected and non-affected family members were included in the analysis of the selected chromosome 19 markers (Table 1). When analyzing only affected members (Table 1, part a), combined data showed a maximum lod score of 6.55 at $\theta=0.03$ with D19S226 (AFM 256yc9). The lod score was 4.18 at $\theta=0.05$ (1 recombinant: II-12) in family 1, and 2.54 at $\theta=0$ in family 2. The lod scores increased considerably when the non-affected family members were included (Table 1, part b). The maximum combined lod score was 8.24 at $\theta=0.03$ with D19S221 (AFM 224yc9) even though the lod score for the second family declined slightly because of an unaffected individual (III-11) who has inherited the disease-associated allele. These results provide strong evidence for a single disease locus in the two families. Varying the penetrances or estimating the marker allele frequencies for the FHM data did not affect these results significantly.

Multipoint Analysis

Figure 3:
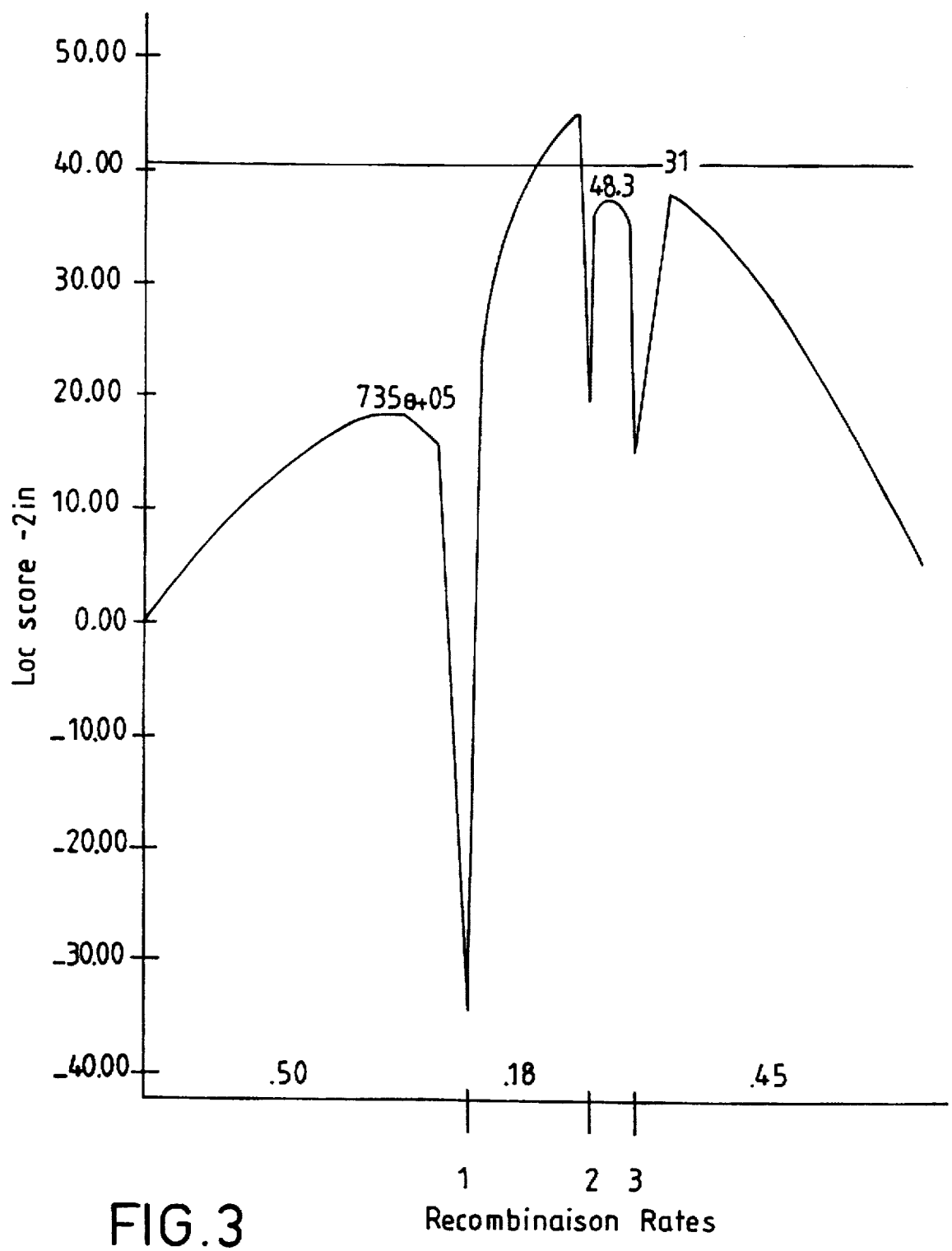
FIG. 3: Multipoint linkage analysis. Location scores for the FHM locus with respect to D19S216 (1), D19S221 (2), D19S226 (3). The solid line indicates the 10:1 odds (1-lod-unit) interval for the placement of the locus. Odds against alternatives are shown for the most likely placements of FHM locus in each interval from the map.
Figure 4:
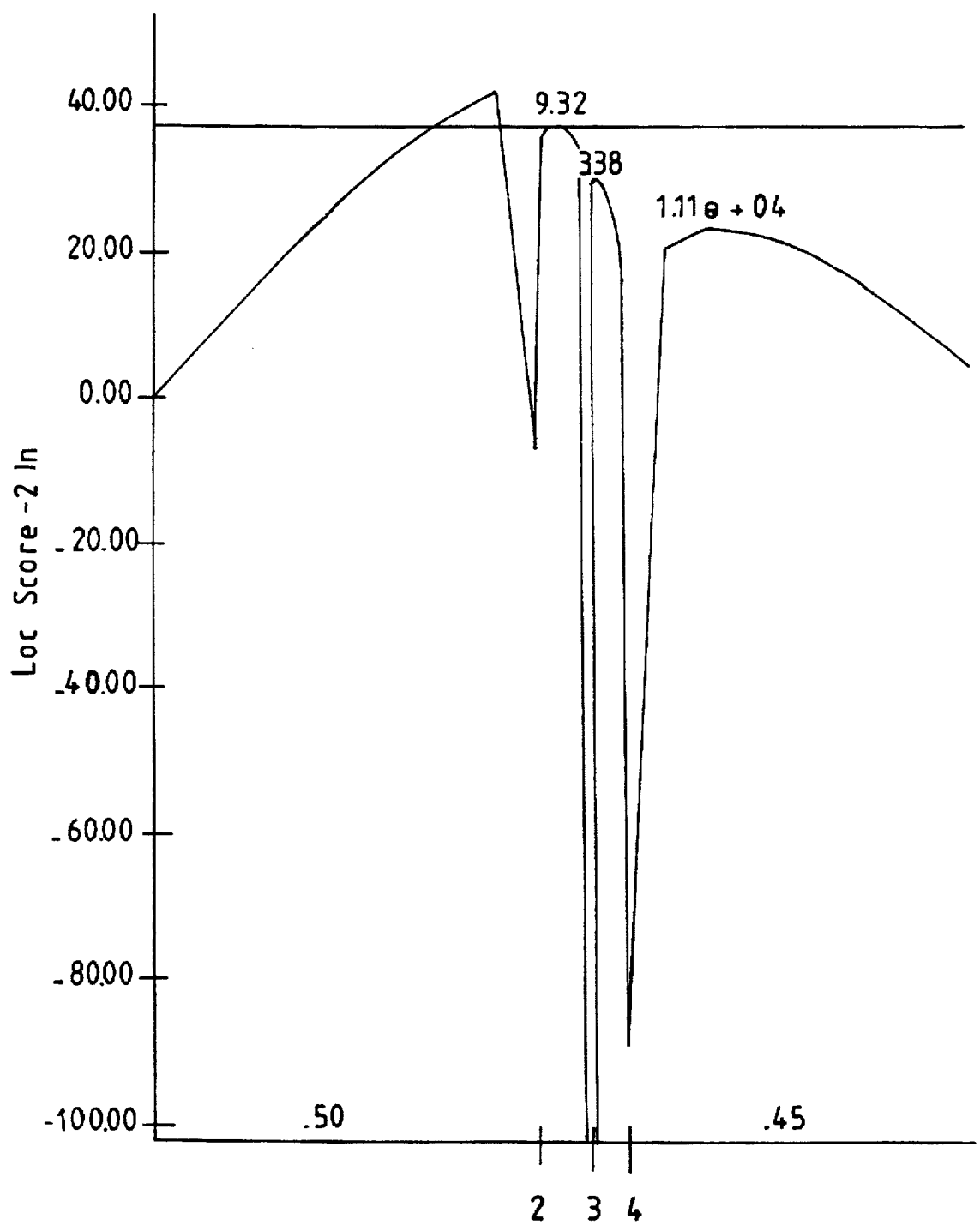
FIG. 4: analogous to FIG. 3, but with respect to D19S221 (2), D19S226 (3) and D19S215 (4).

The order and sex-average recombination fractions between the marker loci estimated from genotype data on a subset of CBPH families are: D19S216—0.18—D19S221—0.07—D19S226—0.05—D19S215 (Weissenbach, J. et al., Nature 359, 794–801, 1992). Due to computational limitations, multilocus linkage analysis was undertaken with subsets of three marker loci considered simultaneously with the FHM or CADASIL locus (Lathrop, G. M. et al., Am. J. Hum. Genet. 37, 482–498, 1985). The location scores are reported with the subsets D19S216—D19S221—D19S226 and D19S221—D19S226—D19S215. Penetrance 0.9 for the FHM locus is assumed in the results presented here (FIGS. 3 and 4). Other subsets of the markers, and different penetrances gave similar results, and led to no modification in the conclusions regarding the intervals to which the disease loci were assigned. As reported previously, significantly greater recombination was found in females compared to males in this region in the CBPH families (Tournier-Lasserve, B. et al., see above). Location score analysis under the assumption of different recombination fractions in males and females led to the same conclusion regarding the locations of the FHM and CADASIL loci (results not shown).

Figure 5:
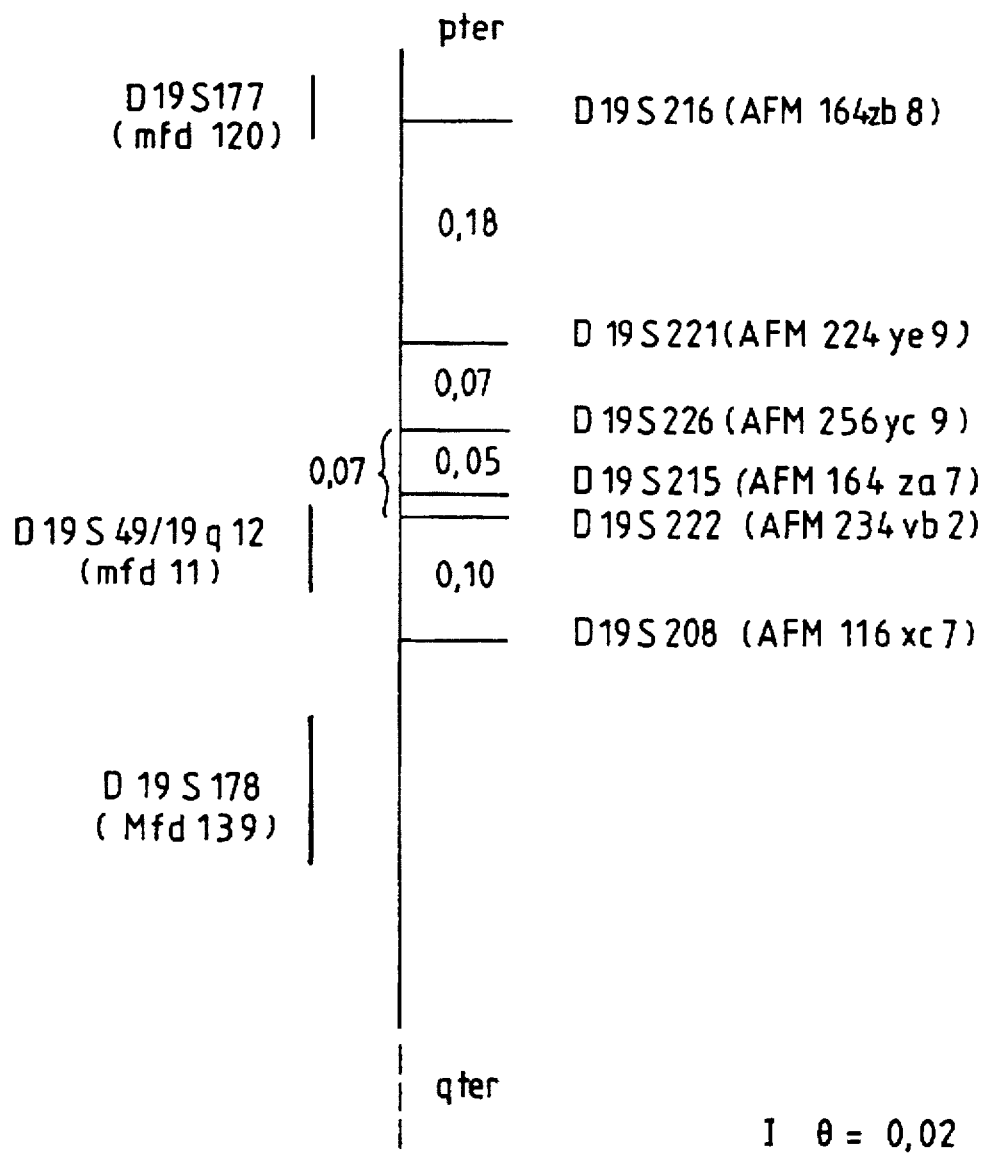
FIG. 5: Genetic regional map of chromosome 19. Critical markers used for linkage analysis are indicated with their respective genetic distances ($\theta$). Map is shown to scale. Approximate location is shown for selected markers from the CBPH database (version 5). The order of the markers was determined as described, in Weissenbach, J & al., Nature 359, 794–801 (1992).

Multilocus linkage analysis provided conclusive evidence that the FHM locus maps in the interior of the region spanned by D19S216—D19S221—D19S226—D19S215 (FIG. 5); the odds against placements outside of D19S216 or D19S215 were greater than $10^4:1$ (FIGS. 3 and 4). The most likely location of the gene was between D19S216 and D19S221, but its placement in the other intervals defined by these markers can not be rejected. The odds against a location within the intervals D19S221—D19S226 and D19S226—D19S215 were 48:1 and 330:1 respectively.

Examination of haplotypes suggested that the evidence for a placement of the FHM locus distal to D19S221 is due largely to a recombination event observed for the chromosome transmitted from individual I-1 to II-12 in the first FHM family. The individual II-12 is affected: her affected father (I-1) is heterozygous for all four of the marker loci. He has had three other affected offsprings who have received the same paternal alleles at the four loci, while individual II-12 has received the same allele of D19S216 but different paternal alleles for the three other loci.

Methodology

Markers. D19S216, D19S221, D19S226, D19S215 were chosen from the microsatellites Genethon linkage map (Weissenbach, J. et al., see above). All oligonucleotides sequences are available in the Genome Data Bank. The number of alleles of the 4 critical markers used for pairwise and multipoint linkage analysis, as well as their respective frequencies were determined in the CBPH Caucasian reference families (Tournier-Lasserve, E. et al., see above).

PCR. Polymorphic genomic sequences were amplified by PCR using a PHC3 Techne apparatus. The reactions were performed in a final volume of 50 μl containing 200 ng of genomic DNA, 125 μM 4dNTP mix, 1×PCR Boehringer Taq Polymerase buffer, 1U Boehringer Taq Polymerase, 1 μM of each primer. Samples were processed through 30 temperature cycles (1st cycle, 94° C. for 5 min; 28 cycles including a denaturation step at 92° C. for 1 min, an annealing step at 55° C. for 1 min and an extension at 72° C. for 10 min).

After addition of 75 μl of loading buffer the samples were denatured for 10 min at 94° C., then laid on a 6% acrylamide DNA sequencing gel. After blotting, nylon membranes were fixed in 0.4M sodium hydroxyde and hybridized with a (CA)12, P32 labelled probe for 14 hours.

Linkage analysis. Two point and multipoint linkage analysis were performed using the LINKAGE package assuming an autosomal dominant FHM gene with a 0.0001 frequency. To test the effects of penetrance on the results, the linkage analysis was performed with penetrances of 0.8, 0.9 and 1.0. Lod scores were calculated at various recombination fractions for each marker.

Protocol of the Diagnosis

The protocol which will be described hereinafter is given by way of example and as such is not considered as limitative. On the basis of the polymorphisms disclosed therein, all known methods of genotype diagnosis are applicable.

Protocol:

Obtaining DNA from the available family members whose status with respect to the disease is known; the nuclear DNA can for example be isolated from peripheral blood leucocytes, lymphoblastoid cell lines, cultured amniotic fluid cells, or chorionic villi, by standard proteinase K treatment and phenolchlorophorm extraction techniques, and amplified or digested with the appropriate restriction enzymes if needed.

Hybridyzing the selected set of primers to the DNA. All oligonucleotide sequences serving as primers are available in the Genome Data Bank.

Amplifying the polymorphic alleles by the PCR technique, using advantageously an automatic thermocycler apparatus such as the PHC3 Techne apparatus. See for example paragraph PCR in Methodology—Analyzing the size of the amplification products (amplimers), for example by electrophoresis on denaturating acrylamid DNA sequencing gel, blotting on Nylon membranes, hybridyzing with radiolabelled suitable repeats probes.

Alternatively, restriction polymorphic fragments can be analyzed on agarose gels after Southern blotting.

Data obtained from autoradiographies are computed and Lod-score calculations are carried out using the M-LINK program.

The assertion of linkage or absence of linkage is derived from statistical analysis, a Lod-score above 3 establishing unambiguous linkage of the disease gene to the tested marker. See above a lod-score <−2 excluding linkage.

Determination of the most informative polymorphims (microsatellites) for the studied family.

When an at risk individual from an affected family is to be tested for predictive diagnosis, the protocol can be completed in the following manner:

Obtaining DNA from the individual in the same manner than above.

Hybridyzing the selected set of primers to the DNA.
Amplifying as above.
Analyzing the amplification products as above.
Using linked polymorphic markers, a DNA based carrier risk can be calculated using the M-LINK program.

The same method can be used for prenatal carrier risk diagnosis.

TABLE 1

Pairwise linkage data for FHM and chromosome 19 markers

| Locus | | Recombination fraction | | | | | | Z max | θ |
|---|---|---|---|---|---|---|---|---|---|
| | | 0.00 | 0.05 | 0.10 | 0.20 | 0.30 | 0.40 | | |
| | | a Affected subjects only | | | | | | | |
| D19S216 | Family 1 | −99.00 | 1.26 | 1.55 | 1.49 | 1.12 | 0.59 | 1.58 | 0.13 |
| | Family 2 | −99.00 | −1.39 | −0.91 | −0.49 | −0.25 | −0.09 | — | — |
| | Total | −99.00 | −0.13 | 0.64 | 1.00 | 0.87 | 0.50 | 1.00 | 0.21 |
| D19S221 | Family 1 | 1.34 | 3.63 | 3.49 | 2.86 | 2.00 | 0.99 | 3.63 | 0.05 |
| | Family 2 | 2.40 | 2.17 | 1.93 | 1.42 | 0.90 | 0.40 | 2.40 | 0.00 |
| | Total | 3.74 | 5.80 | 5.42 | 4.28 | 2.90 | 1.39 | 5.83 | 0.03 |
| D19S226 | Family 1 | 1.94 | 4.18 | 3.99 | 3.24 | 2.25 | 1.13 | 4.18 | 0.05 |
| | Family 2 | 2.54 | 2.31 | 2.06 | 1.52 | 0.96 | 0.42 | 2.54 | 0.00 |
| | Total | 4.48 | 6.49 | 6.05 | 4.76 | 3.22 | 1.55 | 6.55 | 0.03 |
| D19S215 | Family 1 | −2.13 | 2.84 | 2.99 | 2.63 | 1.92 | 1.01 | 2.99 | 0.09 |
| | Family 2 | −99.00 | −1.08 | −0.56 | −0.14 | 0.02 | 0.05 | — | — |

TABLE 1-continued

Pairwise linkage data for FHM and chromosome 19 markers

| Locus | | Recombination fraction | | | | | | Z max | θ |
|---|---|---|---|---|---|---|---|---|---|
| | | 0.00 | 0.05 | 0.10 | 0.20 | 0.30 | 0.40 | | |
| | Total | −99.00 | 1.76 | 2.43 | 2.49 | 1.94 | 1.06 | 2.58 | 0.15 |
| | b Affected and healthy subjects (penetrance = 0 9) | | | | | | | | |
| D19S216 | Family 1 | −6.47 | 1.25 | 1.68 | 1.72 | 1.35 | 0.74 | 1.78 | 0.15 |
| | Family 2 | −4.30 | −1.40 | −0.91 | −0.49 | −0.25 | −0.09 | — | — |
| | Total | −10.77 | −0.15 | 0.77 | −1.23 | −1.10 | 0.65 | 1.80 | 0.22 |
| D19S221 | Family 1 | 0.75 | 6.33 | 5.96 | 4.81 | 3.38 | 1.70 | 6.36 | 0.03 |
| | Family 2 | 1.91 | 1.83 | 1.68 | 1.30 | 0.85 | 0.39 | 1.91 | 0.00 |
| | Total | 2.66 | 8.16 | 7.64 | 6.11 | 4.23 | 2.09 | 8.24 | 0.03 |
| D19S226 | Family 1 | 0.35 | 6.06 | 5.78 | 4.73 | 3.35 | 1.70 | 6.07 | 0.04 |
| | Family 2 | 2.06 | 1.97 | 1.81 | 1.40 | 0.91 | 0.41 | 2.06 | 0.00 |
| | Total | 2.41 | 8.03 | 7.59 | 6.13 | 4.26 | 2.11 | 8.07 | 0.03 |
| D19S215 | Family 1 | −4.71 | 4.72 | 4.78 | 4.12 | 3.02 | 1.60 | 4.81 | 0.08 |
| | Family 2 | −7.86 | −1.42 | −0.81 | −0.26 | −0.03 | 0.04 | — | — |
| | Total | −12.57 | 3.30 | 3.97 | 3.86 | 2.99 | 1.56 | 4.07 | 0.14 |

We claim:

1. Method for screening for familial hemiplegic migraine which comprises searching for the presence of genetic abnormalities via polymorphic analysis linked to familial hemiplegic migraine on the chromosome 19, in the region comprised between the microsatellites D19S216 and D19S215, of a family or of an at risk individual, including fetus.

2. The method according to claim 1, wherein the microsatellites used are chosen among the group consisting of: D19S216, D19S76, D19S221, D19S179, D19S226, D19S252, D19S253, D19S244, D19S415, D19S199, D19S215.

3. A method for screening for familial hemiplegic migraine which comprises selecting polymorphisms via linkage analysis within microsatellite regions responsible for familial hemiplegic migraine on chromosome 19 with the aid of DNA probes to a linkage analysis with the microsatellites D19S216, D19S76, D19S221, D19S179, D19S226, D19S252, D19S253, D19S244, D19S415, D19S199 and D19S215.

4. Method for screening for a subgroup of familial hemiplegic migraine linked to chromosome 19 by a family or an at risk individual, including a fetus, comprising the step of searching for a genetic linkage between DNA polymorphisms and a mutated region linked to the familial hemiplegic migraine, these DNA polymorphisms being located in the region of the chromosome 19 comprised between the microsatellites D19S216 and D19S215, including these microsatellites.

5. The method according to claim 4, wherein the method is first applied on members of a family whose status for familial hemiplegic migraine is known, including ill and healthy members, comprising the steps of determining if the family is linked to abnormalities on chromosome 19, determining the DNA polymorphisms which are the best informatives for the family, choosing primer pairs to the above-determined DNA polymorphisms, amplifying DNA fragments from an at risk individual to be tested and pertaining to this family with the selected primer pairs, and determining if this at risk individual is carrying the affected or healthy polymorphisms and calculating the risk of this individual having inherited the affected region.

* * * * *

UNITED STATES PATENT AND TRADEMARK OFFICE
CERTIFICATE OF CORRECTION

PATENT NO.   : 5,714,319
DATED        : February 3, 1998
INVENTOR(S)  : Joutel et al It is certified that error appears in the above-indentified patent and that said Letters Patent is hereby corrected as shown below:

On the title page
Item [73] should read as follows:

--[73] Assignees: Institut National de la Sante et de la Recherche Medicale, Paris, France and
L'Assistance Publique - Hopitaux de Paris, Paris, France Signed and Sealed this Thirtieth Day of March, 1999

Attest:

Q. TODD DICKINSON

Attesting Officer

Acting Commissioner of Patents and Trademarks